United States Patent [19]
Das

[11] Patent Number: 5,888,743
[45] Date of Patent: Mar. 30, 1999

[54] IN VITRO METHOD FOR DIAGNOSING BENIGN BARRETT'S EPITHELIUM

[76] Inventor: Kiron M. Das, 25 Darren Wood Dr., Martinsville, N.J. 08836

[21] Appl. No.: 493,865

[22] Filed: Jun. 23, 1995

Related U.S. Application Data

[63] Continuation of Ser. No. 257,238, Jun. 9, 1994, abandoned, which is a continuation of Ser. No. 110,484, Aug. 23, 1993, abandoned, which is a continuation of Ser. No. 869,324, Apr. 15, 1992, abandoned, which is a continuation-in-part of Ser. No. 841,653, Feb. 20, 1992, abandoned, which is a continuation-in-part of Ser. No. 341,241, Apr. 19, 1989, abandoned, which is a continuation of Ser. No. 41,937, Apr. 24, 1987, abandoned.

[51] Int. Cl.$^6$ .................................................. G01N 33/53
[52] U.S. Cl. ........................ 435/7.1; 530/388.8; 436/813
[58] Field of Search .............................. 435/7.1, 7.5, 7.9, 435/28, 188, 960; 436/64, 126, 813; 530/388.8

[56] References Cited

U.S. PATENT DOCUMENTS 4,280,954  7/1981  Yannas et al. ........................ 260/123.7

OTHER PUBLICATIONS

Shin et al "Expression of a New Mucin–Type Glycoprotein in Select Epithelial Dysplasias and Neoplasms Detected Immunocytochemically with Mab A–80" APMIS 97:1053–67 1989.

Bancroft & Cook, ed. *Manual of Histological Techniques*, 1984 Churchill Livingstone pp. 197–202.

Abstract No. 44, *The American Journal of Gastroenterology*, vol. 86, p. 1301 (1991).

K.M. Das et al., "A Shared and Unique Epitope(s) on Human Colon, Skin, and Biliary Epithelium Detected by a Monoclonal Anitbody", *Gastroenterology* vol. 98, pp. 464–469 (1990).

Takahashi et al. "Circulating Anitbodies Against Human Colonic Extract Enriched With a 40 kDa Protein In Patients With Ulcerative Colitis", *Gut*, vol. 31, No. 9, pp. 1016–1020 (Sep. 1990).

Robertson et al., "Screening for Colonic Cancer in Patients With Barrett's Esophagus", *Brit. Med. J.*, vol. 298 (6674), p. 650 (1989).

Levine et al., "Specialized Metaplastic Columnar Epithelium in Barrett's Esophagus", *Lab Inves.*, vol. 60, pp. 418–432 (1989).

Das et al., "The Production and Characterization of Monoclonal Antibodies to a Human Colonic Antigen Associated With Ulcerative Colitis: Cellular Localization of the Antigen by Using the Monoclonal Antibody", *Journal of Immunology*, vol. 139, No. 1 pp. 77–84 (Jul. 1, 1987).

Zwas et al., "Scanning Electron Microscopy of Barrett's Epithelium and its Correlation With Light Microscopy and Mucin Stains", *Gastroenterology*, vol. 90, pp. 1931–1941 (1986).

Cameron et al., "The Incidence of Adencarcinoma in Columnar–Lined (Barrett's) Esophagus", *N. Eng. J. Med.*, vol. 313, pp. 857–859 (1985).

Sontag et al., "Barrett's Esophagus and Colonic Tumors", *Lancet*, vol. 1, pp. 946–948 (1985).

Takahashi et al., "Isolation and Characterization of a Colonic Autoantigen Spicifically Recognized by Colon Tissue–Bound IgG from Idiopathic Ulcerative Colitis", *J. Clin. Invest.*, vol. 76, pp. 311–318 (Jul., 1985).

*Primary Examiner*—Lila Feisee
*Assistant Examiner*—Julie E Reeves

[57] ABSTRACT

This invention relates to a method for the diagnosis of benign Barrett's Epithelium and Barrett's-derived adenocarcinoma. The method of diagnosis comprises contacting a monoclonal antibody which reacts with benign Barrett's Epithelium cells and Barrett's-derived adenocarcinoma cells, but does not react with normal esophageal epithelium cells, squamous carcinoma cells, cardia cells or gastric mucosa cells and detecting immunoreactivity. Immunoreactivity indicates a positive diagnosis Barrett's Epithelium or Barrett's-derived adenocarcinoma.

11 Claims, 4 Drawing Sheets

Fig. 3A Fib.3B

Fig. 4A                    Fib.4B

IN VITRO METHOD FOR DIAGNOSING BENIGN BARRETT'S EPITHELIUM

This application is a continuation of application Ser. No. 08/257,238, filed 9 Jun., 1994, now abandoned, which application is a continuation of application Ser. No. 08/110,484, filed on 23 Aug. 1993, now abandoned, which application is a continuation of application Ser. No. 07/869,324, filed on 15 Apr. 1992, now abandoned, which application is a continuation-in-part of application Ser. No. 07/841,653, filed on 20 Feb. 1992, now abandoned, which application is a continuation-in-part of application Ser. No. 07/341,241, filed on 19 Apr. 1989, now abandoned which application is a continuation of application Ser. No. 07/041,937, filed on 24 Apr. 1987 now abandoned.

STATEMENT OF GOVERNMENT INTEREST

This invention was made with government support under NIH Grant No. NIADDK RO1 DK 44314-01. The government has certain rights in this invention.

FIELD OF THE INVENTION

This invention relates to methods for diagnosing Barrett's Epithelium and Barrett's-derived adenocarcinoma. Specifically, this invention relates to the use of monoclonal antibody which reacts with benign Barrett's Epithelium and Barrett's-derived adenocarcinoma cells, but does not react with normal esophageal epithelium (squamous cells), squamous carcinoma cells, cardiac cells or gastric mucosa cells for the diagnosis of benign Barrett's Epithelium and Barrett's-derived adenocarcinoma, as well as for the screening of dysplasia. One such monoclonal antibody is $7E_{12}H_{12}$, which antibody is also reactive with proteins found in colonic epithelial cells.

BACKGROUND OF THE INVENTION

Barrett's Epithelium arises as a complication of chronic reflux esophagitis. In approximately 80% of the cases where chronic reflux esophagitis exists, Barrett's Epithelium arises. In Barrett's Epithelium, the typical stratified squamous epithelium may be replaced by metaplastic columnar epithelial cells. Hence, Barrett's Epithelium predisposes a patient to esophageal carcinoma (Barrett's-derived adenocarcinoma). Barrett's-derived adenocarcinoma develops in approximately 8–15% of all people who have Barrett's Epithelium. See Cameron, et al., "The Incidence of Adenocarcinoma in Columnar-Lined (Barrett's) Esophagus", *N. Eng. J. Med.*, Vol. 313, p. 857–859 (1985).

During the development of Barrett's Epithelium, gastric mucosa extends to the distal esophagus. The morphology of gastric mucosa blends with the transitional zone of Barrett's Epithelium. Because it is difficult to distinguish between gastric mucosa and Barrett's Epithelium, it has been difficult to positively diagnose Barrett's Epithelium. In some cases, cardiac tissue (i.e., tissue from the opening at the upper end of the stomach that connects the stomach and the esophagus) extends to the distal esophagus. This further complicates the diagnosis of Barrett's Epithelium because columnar epithelial cells line the cardiac mucosa. In addition, when cardiac adenocarcinoma extends to the distal esophagus, the histology of the cardiac adenocarcinoma cells resembles Barrett's-derived adenocarcinoma cells, and may be indistinguishable therefrom.

In the past, attempts have been made utilizing enzymatic, histologic and electronmicroscopic features to distinguish Barrett's Epithelium from cardiac cells. However, there has been little success in this area. See Levine, et al., "Specialized Metaplastic Columnar Epithelium in Barrett's Esophagus", *Lab Invest.*, Vol. 60, p. 418–432 (1989). As a result, the diagnosis of benign Barrett's Epithelium and Barrett's-derived adenocarcinoma remain a difficult task, both clinically and pathologically.

It was previously reported that there was a higher frequency of colonic malignancy in patients with Barrett's Esophagus than in a control population. See Sontag, et al., "Barrett's Esophagus and Colonic Tumors", *Lancet*, Vol. 1, p. 946–948 (1985) and Robertson, et al., "Screening for Colonic Cancer in Patients with Barrett's Esophagus", *Brit. Med. J.*, Vol. 298 (6674), p. 650 (1989). However, it has since been discovered that this is not true. See Abstract No. 44, *The American Journal of Gastroenterology*, Vol. 86, p. 1301 (1991). In this abstract, Post, et al. conclude that there is no higher prevalence of colonic neoplasis in patients with Barrett's Esophagus than in asymptomatic controls. Therefore, Barrett's Esophagus does not justify colonoscopic surveillance programs. Hence, the prior literature teaches that there is no relationship between colon cancer and esophageal cancer.

Ulcerative Colitis is an autoimmune disease characterized by diarrhea, rectal bleeding, at times fever, loss of weight and chronic ill health. The disease is characterized by acute exacerbation and remission. To date, there is no indication of any relationship between Barrett's Epithelium and Ulcerative Colitis.

The inventor, while studying the pathogenesis of the autoimmune disease Ulcerative Colitis, purified proteins from colon epithelial cell extracts. While studying these colonic epithelial proteins, the inventor developed a monoclonal antibody reactive with such proteins. This monoclonal antibody was designated $7E_{12}H_{12}$. The hybridoma secreting the $7E_{12}H_{12}$ monoclonal antibody is on deposit with the American Type Culture Collection, Rockville, Md., and is catalogued as ATCC #HB9397. See U.S. patent application Ser. No. 07/841,653 filed Feb. 20, 1992 and Takahashi, F. and Das K. M., "Isolation and Characterization of a Colonic Autoantigen Specifically Recognized by Colon Tissue-Bound Immunoglobulin G From Idiopathic Ulcerative Colitis", *J. Clin. Invest.*, Vol. 76, p. 311–318 (1985).

The inventor has now discovered that the $7E_{12}H_{12}$ monoclonal antibody, which is reactive with colonic epithelial proteins, is also reactive with benign Barrett's Epithelium and Barrett's-derived adenocarcinoma, but not with normal esophageal epithelium cells, squamous carcinoma cells, cardia cells, gastric mucosa cells or small intestinal epithelium.

Because the inventor has discovered that colonic epithelium of patients with Ulcerative Colitis, benign Barrett's Epithelium and Barrett's-derived adenocarcinoma cells all share a common epitope, it is now possible to use the $7E_{12}H_{12}$ monoclonal antibody and other mononoclonal antibodies which recognize the common epitope to diagnose both benign Barrett's Epithelium and Barrett's-derived adenocarcinoma.

It is therefore an object of this invention to provide a method for diagnosing benign Barrett's Epithelium.

It is another object of this invention to provide a method for diagnosing benign Barrett's Epithelium utilizing monoclonal antibody which reacts with benign Barrett's Epithelium but not with normal esophageal epithelium cells, squamous carcinoma cells, cardia cells or gastric mucosa cells.

It is still another object of this invention to provide a method for diagnosing benign Barrett's Epithelium utilizing monoclonal antibody $7E_{12}H_{12}$ which reacts with benign Barrett's Epithelium but not with normal esophageal epithelium cells, squamous carcinoma cells, cardia cells or gastric mucosa cells.

It is a further object of this invention to provide a method for diagnosing Barrett's-derived adenocarcinoma.

It is a still further object of this invention to provide a method for diagnosing Barrett's-derived adenocarcinoma utilizing monoclonal antibody which reacts with Barrett's-derived adenocarcinoma but not with normal esophageal epithelium cells, squamous carcinoma cells, cardia cells or gastric mucosa cells.

It is yet a further object of this invention to provide a method for diagnosing Barrett's-derived adenocarcinoma utilizing monoclonal antibody $7E_{12}H_{12}$ which reacts with Barrett's-derived adenocarcinoma but not with normal esophageal epithelium cells, squamous carcinoma cells, cardia cells or gastric mucosa cells.

It is still another object of this invention to provide a method for screening for dysplasia, a condition which indicates a patient's predisposition for Barrett's-derived adenocarcinoma.

It is yet another object of this invention to provide a method for diagnosing benign Barrett's Epithelium and Barrett's-derived adenocarcinoma utilizing an antibody which recognizes an epitope common to colonic epithelium and Barrett's Epithelium.

It is another object of this invention to provide a method for diagnosing benign Barrett's Epithelium and Barrett's-derived adenocarcinoma utilizing an antibody which recognizes an antigen, such antigen also being reactive with monoclonal antibody $7E_{12}H_{12}$.

SUMMARY OF THE INVENTION

This invention relates to the use of monoclonal antibody for the diagnosis of benign Barrett's Epithelium and Barrett's-derived adenocarcinoma. The monoclonal antibody is reactive with benign Barrett's Epithelium and Barrett's-derived adenocarcinoma but not with normal esophageal epithelium cells, squamous carcinoma cells, cardia cells or gastric mucosa cells. One such monoclonal antibody is $7E_{12}H_{12}$. Immunoperoxidase staining, immunofluorescence, immunoelectronmicroscopy or other detection systems may be utilized to identify reactivity between the monoclonal antibody and Barrett's Epithelium as well as Barrett's-derived adenocarcinoma cells.

In order to detect immunoreactivity between such monoclonal antibody and Barrett's Epithelium and Barrett's-derived adenocarcinoma by immunoperoxidase staining, the following steps may be performed: Esophageal tissue suspected of containing Barrett's Epithelium or Barrett's-derived adenocarcinoma is deparaffinized by heating, immersed in xylene to remove paraffin, rehydrated in decreasing concentrations of alcohol and washed in neutral PBS. Next, free aldehydes are reduced. The tissue sections may then be trypsinized. The tissue sections are then sequentially reacted with normal goat serum, a monoclonal antibody which reacts with benign Barrett's Epithelium and Barrett's-derived adenocarcinoma but not with normal esophageal epithelium cells, squamous carcinoma cells, cardia cells or gastric mucosa cells (such as $7E_{12}H_{12}$ monoclonal antibody), washed and incubated with biotinylated goat anti-mouse antibody. Next, the tissues are washed in PBS, incubated with avidin-biotin-peroxidase complex, treated with diaminobenzidine, washed again, mounted, and microscopically examined for reactivity with a monoclonal antibody. Reactivity of the monoclonal antibody with the esophageal tissue cells indicates the presence of either benign Barrett's Epithelium or Barrett's-derived adenocarcinoma.

BRIEF DESCRIPTION OF THE DRAWINGS

The above brief description, as well as further objects and features of the present invention, will be more fully understood by reference to the following detailed description of the presently preferred, albeit illustrative, embodiment of the present invention when taken in conjunction with the accompanying drawings wherein:

FIG. 1 represents the reactivity of the $7E_{12}H_{12}$ monoclonal antibody with Barrett's Epithelium tissue.

FIG. 4A shows low magnification and FIG. 4B shows high magnification.

DETAILED DESCRIPTION OF THE INVENTION

Figure 1A:
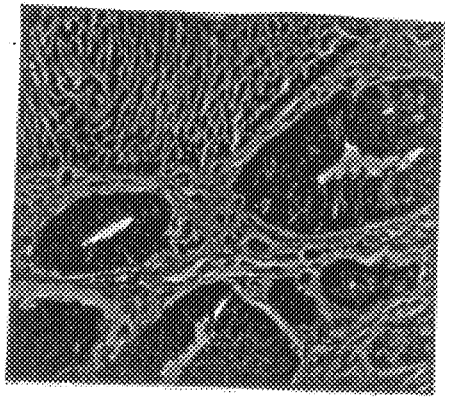
FIG. 1A shows that the monoclonal antibody is reactive with Barrett's tissue in the esophagus taken 32 cm from the patient's lips. The $7E_{12}H_{12}$ monoclonal antibody is not reactive with the adjacent overlying esophageal squamous epithelium (E).

A deposit of monoclonal antibody $7E_{12}H_{12}$ has been made in the American Type Culture Collection, 12301 Parklawn Drive, Rockville, Md. 20852 and the deposited material has been accorded a specific accession number, namely HB9397. This invention is directed to a method for diagnosing benign Barrett's Epithelium (Barrett's Esophagus) and Barrett's-derived adenocarcinoma, as well as to a method for screening for dysplasia. Specifically, this invention is directed to the use of monoclonal antibody which reacts with benign Barrett's Epithelium cells and Barrett's-derived adenocarcinoma cells but not with normal esophageal epithelium cells, squamous carcinoma cells, cardia cells or gastric mucosa cells, to diagnose benign Barrett's Epithelium and Barrett's-derived adenocarcinoma. The monoclonal antibody $7E_{12}H_{12}$, which monoclonal antibody is of the IgM isotype, is an example of such monoclonal antibody. This antibody may be used for immunocytochemical diagnosis of benign Barrett's Epithelium and Barrett's-derived adenocarcinoma. Further, the $7E_{12}H_{12}$ antibody may be used to detect or screen for dysplasia, which is the abnormal development of epithelial tissues, wherein the abnormal development indicates a pre-cancerous state or condition.

Production of the $7E_{12}H_{12}$ Monoclonal Antibody

In order to produce the $7E_{12}H_{12}$ monoclonal antibody of this invention, six-week old BALB/c mice were immunized with an emulsion of 100 µg of a highly enriched Mr 40K protein (1 mg/ml) in an equal volume of complete Freund's adjuvant, given subcutaneously over the neck, in the footpad and intraperitoneally. The Mr 40K protein was purified from human colons. In order to produce the Mr 40K protein, human colon specimens were obtained within one-half hour of surgery for colectomy and stored in negative −80° C. The colon extracts were normal segments which were removed from patients with colon cancer. The colon tissue was then thawed on ice and after removal of fats, the tissue was suspended in 50 ml of a buffer A containing 50 mM Tris HCl pH 8.0, 0.15M NaCl, 2 mM EDTA, 2 mM PMSF and a cocktail of protease inhibitors comprised of Aprotinine 0.3 $\mu$M, Pepstatin 1 $\mu$M, and Leupeptine 1 $\mu$M. The colon tissue was minced with fine scissor and centrifuged at 2,000 g for 10 minutes, and supernatant was discarded. The step was repeated at least 7 times until the supernatant was clear.

Next, 100 ml of buffer B (which is the same as buffer A, except that it contained 10 mM EDTA) was added to the final precipitate, and the precipitate was left on ice for half an hour and then homogenized over ice using a polytron for 5 minutes using 15 second bursts interspersed with one minute intervals. The homogenate was then centrifuged at 10,000 g for 30 minutes. The supernatant was removed and ultracentrifuged at 100,000 g for 90 minutes. Next, the supernatant was frozen and thawed 3 times and centrifuged for 10 minutes at 10,000 g to remove the precipitate. The supernatant was dialyzed against a buffer C containing 20 mM Bis-Tris Propane, pH 6.5 at 4° C.

Next, an ion exchange chromatography was performed using DEAE column. The dialyzed material was delipidated by mixing it with an equal volume of 1,1,2-Trichlorotrifluoroethane, vortexed and centrifuged at 2,000 g×30 minutes. The top aqueous layer was separated, filtered through 0.22 micron syringe filter and used for chromatography. Five mg of sample was loaded and the column was washed with buffer C until O.D. 280 absorption became steady near zero. Then the column was eluted with step gradient of 0.2M 0.35M and 0.48M NaCl in buffer C. Peaks were monitored by O.D. at 280 nm. The peaks were collected separately and dialyzed against a buffer D containing 20 mM phosphate and 0.15M NaCl pH 7.4.

Hydrophobic Interaction Chromatography was then performed using the 0.35M and 0.48M NaCl eluates from the ion-exchange column. A 1×10 cm econo column (Bio-Rad) was packed with 5 ml bed volume of phenyl sepharose and equilibrated with 20 mM phosphate, 0.15M NaCl, pH 7.4 containing 0.8M ammonium sulfate. The protein sample was adjusted to 0.8M ammonium sulfate by addition of solid ammonium sulfate and loaded to the column as 1 mg of protein per ml of bed volume. The column was washed with loading buffer until the O.D. 280 steady near zero. Then, the column was eluted stepwise with 20 m phosphate, 0.15M NaCl, pH 7.4 and then with distilled water.

Next, immunotransblot analysis was performed. Eluted proteins were subject to a 10% SDS polyacrylamide gel electrophoresis and electrophoretically transferred to nitrocellulose paper. The nitrocellulose strips were washed, dried and exposed for autoradiography at −80° C.

After immunizing the mice with the Mr 40K protein emulsion, the mice were given 40 $\mu$g of highly purified Mr 40K protein intraveneously one day prior to fusion. The splenic lymphocytes were mixed with cells of non-secretor BALB/c-derived myeloma line (NSO) in the mid-logarithmic phase of growth in a ratio of 8:1 spleen to myeloma cells. Fusion was performed with a 50% polyethylene glycol (mol. wt. 4,000; Merck, Damstadt, West Germany) using the standard technique.

After fusion, cells were washed once with HAT medium (100 $\mu$M hypoxanthine, 400 nM-aminopterin, 16 $\mu$M-thymidine 20% fetal calf serum, 10% NCTC109, 1% penicillin and streptomycin, 1% non-essential amino acids in DME) and gently resuspended at $5\times10^5$ myeloma cells/ml.

Cultures were set up with 100 $\mu$l of the suspension per well of 96-well flat-bottom plates (Linbro, Flow Laboratories Inc., McLean, Va.). Cultures were maintained at 37° C. in 8% $CO_2$ and screening for antibodies was performed on day 14 by an ELISA. Clonal growth was assessed by inspection. Positive clone were expanded in 24 well flat-bottom microculture plates (Linbro, Flow Laboratories, Inc., McLean, Va.) and cloned in soft agar. Expanded clones were maintained in vitro in 25 $cm^2$ flasks (Corning Glass Works, Corning, N.Y.) or injected intraperitoneally into 2, 6, 10, 14 tetramethylpentadecane (Pristane; Aldrich Chemical Co., Milwaukee, Wis.) -primed BALB/c mice for the production of ascitic fluid. Aliquots of expanded clones were also frozen and stored in liquid nitrogen without subsequent loss of secretory capacity.

Of the monoclonal antibodies produced, the monoclonal antibody designated $7E_{12}H_{12}$ gave the highest reactivity in the ELISA. $7E_{12}H_{12}$ was further purified by subcloning. The hybridoma secreting monoclonal antibody $7E_{12}H_{12}$ is on deposit with the American Type Culture Collection, Rockville, Md., where it was received Apr. 16, 1987 and catalogued as ATCC #HB9397.

This $7E_{12}H_{12}$ monoclonal antibody reacts with colon epithelial cells, biliary epithelium of gallbladder, common bile duct and squamous epithelial of skin. In contrast, the $7E_{12}H_{12}$ monoclonal antibody does not react with esophageal squamous epithelial cells, gastric mucosa and 15 other epithelial organs, including small intestinal enterocytes. See Takahashi, et al., "Isolation and Characterization of Colonic Autoantigen Specifically Recognized by Colon Tissue-Bound Immunoglobulin G from Idiopathic Ulcerative Colitis", *J. Clin. Invest,* Vol. 76, p. 311–318 (1985); Das, et al., "The Production and Characterization of Monoclonal Antibodies to the Human Colonic Antigen Associating with Ulcerative Colitis: Cellular Localization of the Antigen By Using the Monoclonal Antibody", *J. Immunology,* Vol. 139, p. 77–84 (1987); Das, et al., "A Shared and Unique Epitope (s) On Human Colon, Skin and Biliary Epithelium Detected By A Monoclonal Antibody", *Gastroenterology,* Vol. 98, p.464–469 (1990).

As demonstrated herein, the $7E_{12}H_{12}$ monoclonal antibody reacts with benign Barrett's Epithelium, but not with esophageal squamous, gastric and small intestinal epithelium. Further, the monoclonal antibody $7E_{12}H_{12}$ also reacts with Barrett's-derived adenocarcinoma (esophageal carcinoma). Because the $7E_{12}H_{12}$ monoclonal antibody has a high degree of reactivity and specificity to Barrett's Epithelium (benign) and adenocarcinoma derived from Barrett's Epithelium, the $7E_{12}H_{12}$ monoclonal antibody may be used for the identification and diagnosis of Barrett's Epithelium and adenocarcinoma. Further, the $7E_{12}H_{12}$ monoclonal antibody may be used to screen for dysplasia.

Acquisition of Human Esophageal Tissue 22 biopsy specimens from benign Barrett's Esophagus, 12 operative specimens from Barrett's-derived adenocarcinoma, 11 biopsy specimens from normal esophagus, 13 biopsy specimens from squamous cell carcinoma of the esophagus and 9 specimens of cardia (gastroesophageal junction) were examined. The average age of the patients from whom the specimens were obtained was 57 years, ranging from 14 to 85 years, 45 of the specimen subjects being male. The demographic and morphologic characteristics of the patients with Barrett's Esophagus are stated below in Table I.

TABLE I

Demographic and morphologic characteristics of patients with benign Barrett's Epithelium

| Number of Patients | Average Age Range (years) | Sex M:F | Cell Types in the Barrett's Epithelium (Gastric:Intestinal) |
|---|---|---|---|
| 22 | 54 (14–85) | 14:8 | 11:11 |

The esophageal biopsies were taken by different physicians in the GI Division Endoscopy Suite at Robert Wood Johnson University Hospital. The biopsies were fixed immediately in buffered formalin and submitted to the Department of Pathology.

The 12 operative specimens were from patients who had resection of the gastroesophageal region for malignancy (adenocarcinoma and squamous cell carcinoma). All of the tissues were processed by routine methods and the sections were stained with hematoxylin and eosin. Based on the histologic features present, paraffin blocks were further sectioned for studying immunoreactivity against the $7E_{12}H_{12}$ monoclonal antibody by the immunoperoxidase staining methods described below.

Immunoperoxidase Staining

The tissues obtained were sectioned (5 μm), mounted on poly-L-lysine coated slides, deparaffinized by heating at 56° C. for 1 hour, immersed in xylene, rehydrated in 100%, 95%, 70% and 50% alcohol and washed in phosphate buffered saline (PBS), pH 7.2. Free aldehydes were reduced with 0.05% solution borohydride in phosphate buffered saline, pH 7.2 for 30 minutes at 4° C. Sections were trypsinized (1% trypsin plus 1% $CaCl_2$ in phosphate buffered saline) for 15 minutes at 37° C., and washed in phosphate buffered saline for 5 minutes with three changes at 40° C. Sections were then sequentially reacted with 1% normal goat serum for 2 hours, monoclonal antibody $7E_{12}H_2$ at 1:10 to 1:50 dilution overnight at 4° C., washed and incubated with biotinylated goat anti-mouse IgM (Vector Lab, Burlingame, Calif.). The tissues were washed in phosphate buffered saline and then incubated with avidin-biotin-peroxidase complex (ABC, Vector Lab, Burlingame, Calif.) for 90 minutes. The reaction was then developed by treating with 1 mg/ml 3-3' diaminobenzidine (DAB) in 0.1 mol/l-TRIS-HCl buffer, pH 7.6, 0.02% $H_2O_2$ in the dark for 10 minutes. The tissues were then washed, stained in hematoxylin for one minute (for counterstaining), washed, dehydrated in graded (50%, 70%, 90% and 100%) ethanol and then in xylene for 2–3 minutes and mounted with coverslips for microscopic examination.

Results

Table II shows the reactivity of the $7E_{12}H_{12}$ monoclonal antibody with benign Barrett's Epithelium, Barrett's-derived adenocarcinoma, normal esophagus squamous cell epithelium and squamous cell carcinoma.

TABLE II

Results of immunoperoxidase experiments showing reactivity of the $7E_{12}H_{12}$ monoclonal antibody with various esophagus cells.

| Histology | No. Of Specimens | Immunoreactivity With $7E_{12}H_{12}$ | |
|---|---|---|---|
| | | Present | Absent |
| benign Barrett's Epithelium | 22 | 19 | 3 |
| [1]Barrett's-derived adenocarcinoma | 12 | 12 | 0 |
| normal esophagus squamous cell epithelium | 11 | 0 | 11 |
| [2]squamous cell carcinoma | 13 | 1 | 12 |

[1]5 biopsy specimens; 7 esophagectomy specimens
[2]8 biopsy specimens; 5 esophagectomy specimens As shown in Table II, 19 of the 22 Barrett's Epithelium biopsied specimens were reactive with monoclonal antibody $7E_{12}H_{12}$. Among these 19 specimens, 3 biopsies were taken from the mid-esophagus (20 to 25 cm from the lips), 4 were taken from 26 to 30 cm from the lips, and 12 were taken from 31 cm from the lips to the distal esophagus. See Table III below.

TABLE III

Results of immunoperoxidase experiments showing reactivity of the $7E_{12}H_{12}$ monoclonal antibody with Barrett's Epithilium cells.

| Distance of Barrett's Tissue from Oral Cavity | # of Specimens | Immunoreactivity | |
|---|---|---|---|
| | | Absent | Present |
| 20 to 25 cm | 4 | 1 | 3 |
| 26 to 30 cm | 4 | 0 | 4 |
| 31 cm to distal | 14 | 2 | 12 |

The 3 biopsies which did not react with the $7E_{12}H_{12}$ monoclonal antibody included 1 taken from 20 cm from the lips and 2 taken from the distal esophagus, all of which showed cardiac type epithelium.

Figure 1B:
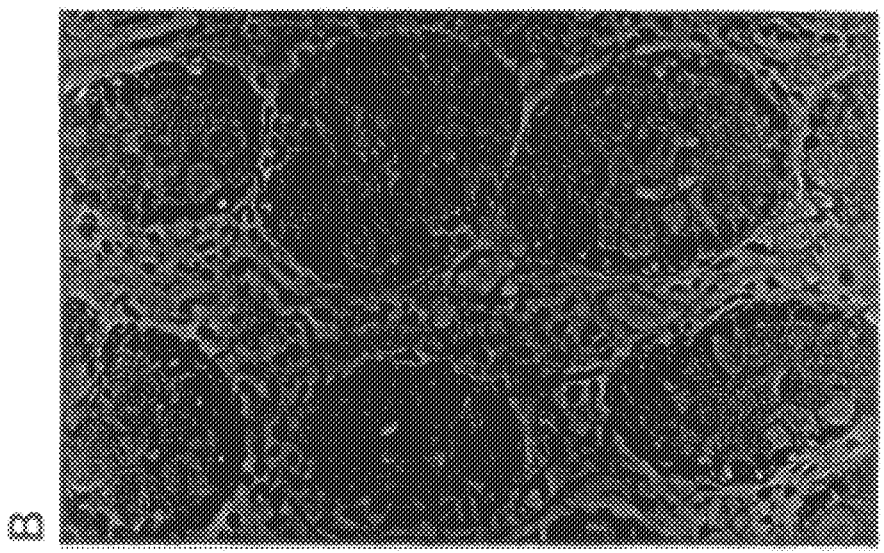
FIG. 1B shows that the $7E_{12}H_{12}$ monoclonal antibody is reactive with Barrett's tissue in the esophagus taken 25 cm from the patient's lips.

FIG. 1 shows the reactivity of the $7E_{12}H_{12}$ monoclonal antibody with Barrett's Epithelium specimens. FIG. 1A shows that the 32 cm Barrett's Epithelium specimens are reactive with monoclonal antibody $7E_{12}H_{12}$, whereas the esophageal squamous (E) was not reactive with the monoclonal antibody. This is shown by hematoxylin counterstaining, wherein the calibration bar was 10 microns. FIG. 1B shows the reactivity of the $7E_{12}H_{12}$ monoclonal antibody with Barrett's Epithelium specimens taken from 25 cm from the lips. Some of the goblet cells present were negative (see arrow-heads). This is also shown by hematoxylin counterstaining wherein the calibration bar was 10 microns.

Figure 2:
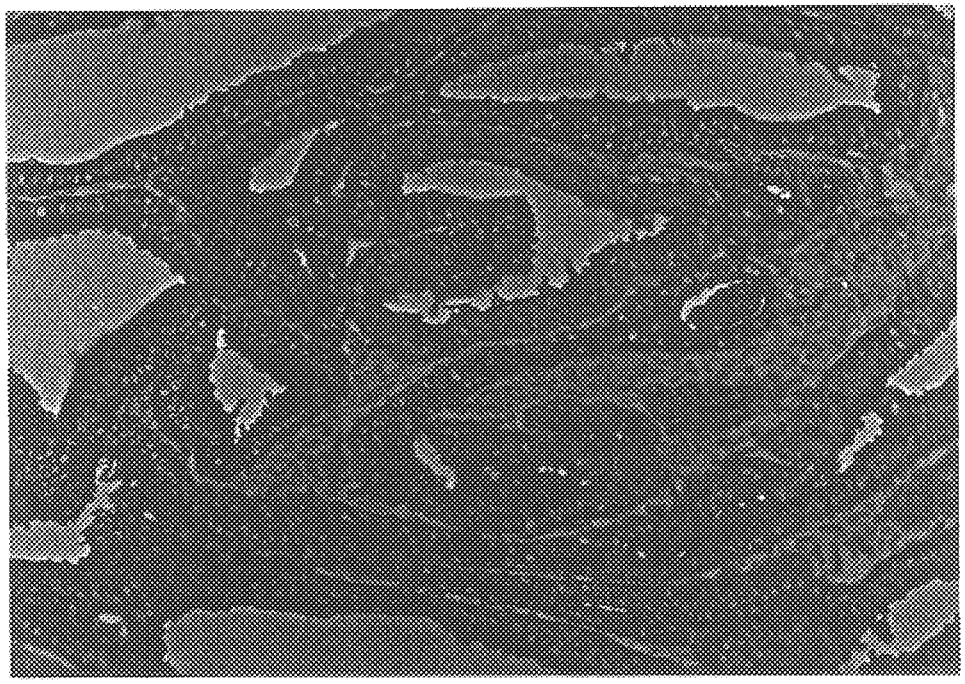
FIG. 2 represents the reactivity of the $7E_{12}H_{12}$ monoclonal antibody with adenocarcinoma cells arising from Barrett's Epithelium.

The staining patterns in the different cell types were homogeneous or granular and mostly cytoplasmic. In some of the Barrett's tissue, the staining was patchy. In contrast, in each of the adenocarcinoma operative specimens, the staining was more intense, reacting with all of the cells of the tumor. FIG. 2 shows the reactivity of the $7E_{12}H_{12}$ monoclonal antibody and Barrett's-derived adenocarcinoma cells. This is shown by hematoxylin counterstaining, wherein the calibration bar was 10 microns. Normal colonic and jejunal biopsy tissue specimens were examined in parallel. While colonic epithelium consistently reacted with monoclonal antibody $7E_{12}H_{12}$ jejunal mucosa did not.

Figure 3:
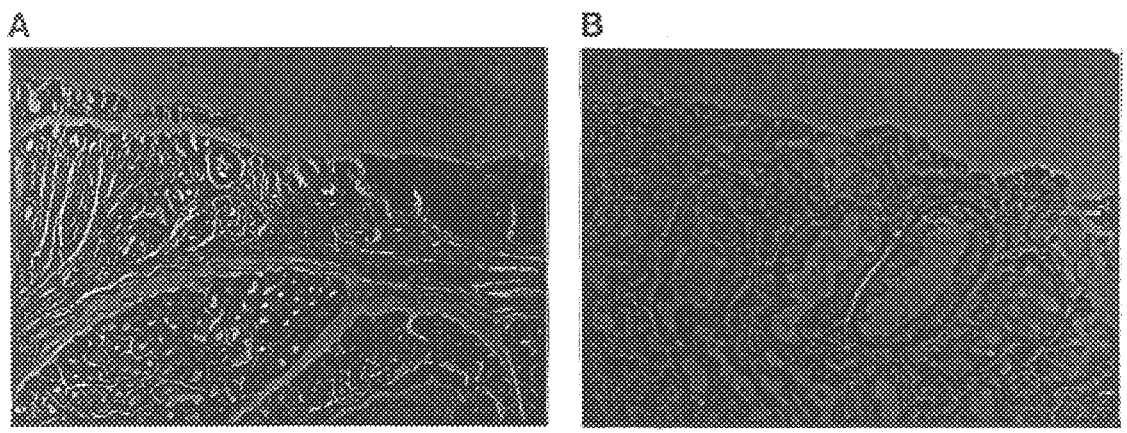
FIG. 3A represents the non-reactivity of the $7E_{12}H_{12}$ monoclonal antibody with normal cardiac epithelium and submucosa glands at the gastroesophageal junction.
FIG. 3B represents the non-reactivity of the $7E_{12}H_{12}$ monoclonal antibody with normal cardiac epithelium.

Nine tissue specimens from gastric cardia were also examined. The cardia is the opening at the upper end of the stomach that connects with the esophagus. All of them were negative. See FIG. 3A. FIG. 3B represents the non-reactivity of monoclonal antibody $7E_{12}H_{12}$ with cardiac epithelium and submucosa glands by hematoxylin and eosin counterstaining, wherein the calibration bar was 10 microns.

Figure 4:
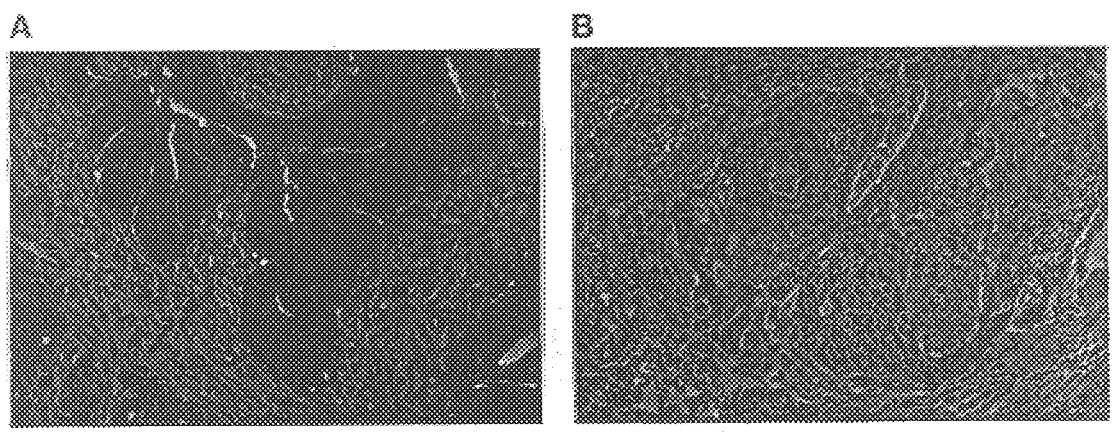
FIG. 4 represents the non-reactivity of the $7E_{12}H_2$ monoclonal antibody with squamous cell carcinoma.

FIG. 4 (panel A shows low magnification and panel B shows high magnification) represents the non-reactivity of the $7E_{12}H_{12}$ monoclonal antibody with squamous cell carcinoma as shown by hematoxylin and eosin counterstaining wherein the calibration bar was 10 microns. Of the 13 esophageal squamous cell carcinomas examined, 12 did not react with monoclonal antibody $7E_{12}H_{12}$. Only 1 squamous cell carcinoma reacted with focal and patchy cytoplasmic staining.

The data presented herein demonstrates that the $7E_{12}H_{12}$ monoclonal antibody reacts with 87% of benign Barrett's tissue, and with 100% of Barrett's-derived adenocarcinoma. As a result, it is now known that colonic and Barrett's Epithelium share a common epitope. The $7E_{12}H_{12}$ monoclonal antibody was not reactive with normal esophageal or jejunal epithelium, as previously reported by Das, et al., "The Production and Characterization of Monoclonal Antibodies to the Human Colonic Antigen Associating with Ulcerative Colitis: Cellular Localization of the Antigen By Using the Monoclonal Antibody", *J. Immunology,* Vol. 139, p. 77–84 (1987). Further, the $7E_{12}H_{12}$ monoclonal antibody does not react with squamous cell carcinoma arising from the esophagus.

In addition, the $7E_{12}H_{12}$ monoclonal antibody is not reactive with mucosa from gastric cardia in both operative and biopsy specimens, clearly showing the transitional zone. With regard to the 3 Barrett's Epithelium specimens which did not react with the $7E_{12}H_{12}$ monoclonal antibody, it is possible that such specimens represent a subgroup of Barrett's Epithelium. As described by Zwas, et al., "Scanning Electron Microscopy of Barrett's Epithelium and its Correlation With Light Microscopy and Mucin Stains", *Gastroenterology,* Vol. 90, p. 1931–1941 (1986), Barrett's Epithelium synthesizes neutral and acid non-sulfated mucin, resembling gastric and intestinal mucin. It is possible that the $7E_{12}H_{12}$ monoclonal antibody could have reacted to colonic type mucin secreting cells in addition to other cell types. Additional studies are necessary to further characterize the individual cell types in Barrett's Epithelium which react with the $7E_{12}H_{12}$ monoclonal antibody.

Because the $7E_{12}H_{12}$ monoclonal antibody reacts with colonic epithelium, Barrett's Epithelium and Barrett's-derived adenocarcinoma, but does not react with normal squamous epithelium, squamous carcinoma, cardiac cells or small intestinal enterocytes, the $7E_{12}H_{12}$ monoclonal antibody is an identifying marker for Barrett's Epithelium and Barrett's-derived adenocarcinoma. Hence, the $7E_{12}H_{12}$ monoclonal antibody may be used to diagnose benign Barrett's Epithelium and Barrett's-derived adenocarcinoma in the esophagus. In addition, because dysplasia indicates the presence of a pre-adenocarcinoma condition, the $7E_{12}H_{12}$ monoclonal antibody may be used to screen for dysplastic cells, thus indicating predisposition for adenocarcinoma before its actual manifestation.

Further, antibodies, including monoclonal antibodies, which react with Barrett's Epithelium and Barrett's-derived adenocarcinoma, but not with normal esophageal squamous epithelium cells, squamous carcinoma cells, cardiac cells or gastric mucosa cells may be used to diagnose Barrett's Epithelium and Barrett's-derived adenocarcinoma. Antibodies which recognize the epitope common to colonic epithelium and Barrett's Epithelium, or antibodies which recognize an antigen, such antigen also being reactive with monoclonal antibody $7E_{12}H_{12}$, may be used to diagnose Barrett's Epithelium and Barrett's-derived adenocarcinoma.

Although the invention herein has been described with reference to particular embodiments, it is to be understood that these embodiments are merely illustrative of the various aspects of this invention. Thus, it is to be understood that various modifications may be made in the illustrative embodiments and other arrangements may be devised without departing from the spirit and scope of this invention.

What is claimed is:

1. An in vitro method for diagnosing benign Barrett's Epithelium which comprises contacting esophageal tissue suspected of containing Barrett's Epithelium cells with the monoclonal antibody $7E_{12}H_{12}$ which is produced by the hybridoma deposited under ATCC accession number HB 9397, which reacts with benign Barrett's Epithelium cells but does not react with normal esophageal epithelium cells, squamous carcinoma cells, cardia cells or gastric mucosa cells and detecting immunoreactivity between the esophageal tissue and the monoclonal antibody, such immunoreactivity indicating a positive diagnosis of benign Barrett's Epithelium.

2. The method according to claim 1 wherein detecting immunoreactivity is performed by immunoperoxidase staining, immunofluorescence or immunoelectronmicroscopy.

3. The method according to claim 2 wherein the immunoperoxidase staining comprises:

(a) deparaffinizing the esophageal tissue by heating;

(b) immersing the deparaffinized tissue in xylene;

(c) rehydrating the tissue in decreasing concentrations of alcohol;

(d) washing the rehydrated tissue in neutral PBS;

(e) reducing the aldehydes of the washed tissue of step (d);

(f) reacting the tissue with normal goat serum, the monoclonal antibody, biotinylated goat anti-mouse antibody and avidin-biotin-peroxidase complex;

(g) treating the reacted tissue with diaminobenzidine;

(h) washing the diaminobenzidine-treated tissue;

(i) staining the washed tissue of step (h) with hematoxylin, eosin or both; and (j) examining the stained tissue under a microscope to detect the presence of immunoreactivity.

4. The method according to claim 3 which further comprises the step of trypsinizing the esophageal tissue after reducing the aldehydes in the tissue but before reacting the tissue with the goat serum, monoclonal antibody, biotinylated goat anti-mouse antibody and avidin-biotin-peroxidase complex.

5. The method according to claim 3 wherein the decreasing concentrations of alcohol used for rehydration are 100%, 95%, 70% and 50% alcohol.

6. An in vitro method for diagnosing benign Barrett's-derived adenocarcinoma which comprises contacting esophageal tissue suspected of containing Barrett's-derived adenocarcinoma cells with the monoclonal antibody $7E_{12}H_{12}$ which is produced by the hybridoma deposited under ATCC accession number HB 9397, which reacts with Barrett's-derived adenocarcinoma cells but does not react with normal esophageal epithelium cells, squamous carcinoma cells, cardia cells or gastric mucosa cells and detecting immunoreactivity between the esophageal tissue and the monoclonal antibody, such immuno-reactivity indicating a positive diagnosis of benign Barrett's-derived adenocarcinoma.

7. The method according to claim 6 wherein detecting immunoreactivity is performed by immunoperoxidase staining, immunofluorescence or immunoelectronmicroscopy.

8. The method according to claim 7 wherein the immunoperoxidase staining comprises:

(a) deparaffinizing the esophageal tissue by heating;

(b) immersing the deparaffinized tissue in xylene;

(c) rehydrating the tissue in decreasing concentrations of alcohol;

(d) washing the rehydrated tissue in neutral PBS;

(e) reducing the aldehydes of the washed tissue of step (d);

(f) reacting the tissue with normal goat serum, the monoclonal antibody, biotinylated goat anti-mouse antibody and avidin-biotin-peroxidase complex;

(g) treating the reacted tissue with diaminobenzidine;

(h) washing the diaminobenzidine-treated tissue;

(i) staining the washed tissue of step (h) with hematoxylin, eosin or both; and (j) examining the stained tissue under a microscope to detect the presence of immunoreactivity.

9. The method according to claim 8 which further comprises the step of trypsinizing the esophageal tissue after reducing the aldehydes in the tissue but before reacting the tissue with the goat serum, monoclonal antibody, biotinylated goat anti-mouse antibody and avidin-biotin-peroxidase complex.

10. The method according to claim 8 wherein the decreasing concentrations of alcohol used for rehydration are 100%, 95%, 70% and 50% alcohol.

11. An in vitro method for screening for those forms of esophageal dysplasia that are caused by Barrett's-derived adenocarcinoma, thereby indicating a predisposition for Barrett's-derived adenocarcinoma, which comprises contacting esophageal tissue with the monoclonal antibody $7E_{12}H_{12}$ which is produced by the hybridoma deposited under ATCC accession number HB 9397, which reacts with benign Barrett's Epithelium cells and Barrett's-derived adenocarcinoma cells but does not react with normal esophageal epithelium cells, squamous carcinoma cells, cardia cells or gastric mucosa cells and detecting immunoreactivity between such tissue and such monoclonal antibody, thereby screening for dysplasia.

* * * * *